US008708905B2

(12) United States Patent
Sarkela

(10) Patent No.: US 8,708,905 B2
(45) Date of Patent: Apr. 29, 2014

(54) METHOD, DEVICE AND COMPUTER PRODUCT FOR EEG MONITORING, ANALYSIS AND DISPLAY

(75) Inventor: Mika Sarkela, Espoo (FI)

(73) Assignee: General Electric Company, Schenectady, NY (US)

( * ) Notice: Subject to any disclaimer, the term of this patent is extended or adjusted under 35 U.S.C. 154(b) by 1354 days.

(21) Appl. No.: 12/483,404

(22) Filed: Jun. 12, 2009

(65) Prior Publication Data

US 2010/0317931 A1 Dec. 16, 2010

(51) Int. Cl.
*A61B 5/00* (2006.01)
*A61B 5/0476* (2006.01)
*G06F 19/00* (2011.01)

(52) U.S. Cl.
CPC .............. *G06F 19/30* (2013.01); *G06F 19/34* (2013.01); *G06F 19/3406* (2013.01); *G06F 19/3431* (2013.01); *G06F 19/345* (2013.01); *G06F 19/3487* (2013.01); *A61B 5/0476* (2013.01); *A61B 5/72* (2013.01); *A61B 5/7221* (2013.01); *A61B 5/7235* (2013.01); *A61B 5/743* (2013.01); *A61B 2505/01* (2013.01); *A61B 2505/03* (2013.01); *A61B 2505/05* (2013.01); *Y10S 128/923* (2013.01); *Y10S 128/925* (2013.01)
USPC ........... 600/301; 600/544; 600/545; 128/923; 128/925; 345/418; 345/440; 345/440.1; 382/128; 702/188; 706/2

(58) Field of Classification Search
USPC ................................................ 600/300–301
See application file for complete search history.

(56) References Cited

U.S. PATENT DOCUMENTS

| | | | | |
|---|---|---|---|---|
| 4,579,125 A | * | 4/1986 | Strobl et al. | 600/544 |
| 5,181,520 A | * | 1/1993 | Wertheim et al. | 600/544 |
| 5,262,944 A | * | 11/1993 | Weisner et al. | 600/300 |
| 5,299,118 A | * | 3/1994 | Martens et al. | 600/509 |
| 5,438,983 A | * | 8/1995 | Falcone | 600/301 |
| 5,860,918 A | * | 1/1999 | Schradi et al. | 600/300 |
| 5,907,291 A | * | 5/1999 | Chen et al. | 340/870.16 |
| 5,912,656 A | * | 6/1999 | Tham et al. | 345/418 |
| 5,921,920 A | * | 7/1999 | Marshall et al. | 600/300 |
| 6,067,467 A | | 5/2000 | John | |

(Continued)

FOREIGN PATENT DOCUMENTS

WO WO 2009034507 A2 * 3/2009 ........... A61B 5/0452
WO WO 2009126997 A1 * 10/2009 ............. G06F 19/00

OTHER PUBLICATIONS

European Search Report dated Sep. 9, 2010.

*Primary Examiner* — Gary Jackson
*Assistant Examiner* — Marie Archer
(74) *Attorney, Agent, or Firm* — Andrus Intellectual Property Law, LLP

(57) ABSTRACT

A method, device, and computer program product for monitoring the physiological state of a subject is disclosed. A first plurality of physiological signals are acquired from the subject and a second plurality of signal parameters are determined based on the first plurality of physiological signals. Relevant signal information is selected from among the signal information produced and at least one screen page is displayed at a time, thereby to make at least part of the signal information visible to a user. The signal information visible to the user on the at least one screen page may then be revised based on the selection and without user interaction, thereby to accelerate clinical decision-making and to diminish the possibility of undetected changes in the state of the subject.

15 Claims, 5 Drawing Sheets

(56) References Cited

U.S. PATENT DOCUMENTS

| | | |
|---|---|---|
| 6,188,407 B1 * | 2/2001 | Smith et al. .................. 715/841 |
| 7,460,905 B2 * | 12/2008 | Mase et al. .................. 600/544 |
| 2004/0054261 A1 * | 3/2004 | Kamataki et al. ............. 600/300 |
| 2006/0167368 A1 | 7/2006 | Sarkela |
| 2007/0010795 A1 | 1/2007 | Sarkela et al. |
| 2007/0142873 A1 | 6/2007 | Esteller et al. |
| 2007/0276281 A1 | 11/2007 | Sarkela |
| 2008/0001600 A1 | 1/2008 | deCharms |
| 2008/0021340 A1 | 1/2008 | Sarkela |
| 2008/0167569 A1 | 7/2008 | Ermes et al. |
| 2008/0194981 A1 | 8/2008 | Sarkela et al. |
| 2008/0228100 A1 * | 9/2008 | Navakatikyan ............... 600/544 |
| 2008/0270080 A1 * | 10/2008 | Zong .......................... 702/188 |
| 2008/0281168 A1 * | 11/2008 | Gibson et al. ................. 600/301 |
| 2008/0281170 A1 * | 11/2008 | Eshelman et al. ............. 600/301 |
| 2009/0048530 A1 | 2/2009 | Sarkela et al. |
| 2009/0054743 A1 * | 2/2009 | Stewart ........................ 600/301 |

* cited by examiner

METHOD, DEVICE AND COMPUTER PRODUCT FOR EEG MONITORING, ANALYSIS AND DISPLAY

BACKGROUND OF THE INVENTION

This disclosure relates generally to patient monitoring. More particularly, the present invention relates to patient monitoring and monitors, in which several physiological parameters are derived from a subject and various signal information, such as the time evolutions of the parameters, may be presented to the user. The physiological signal data involved may be, for example, EEG signal data.

Patient monitors are electronic devices designed to display physiological information about a subject. Electrocardiogram (ECG), electroencephalogram (EEG), plethysmographic signals, and signals related to blood pressure, temperature, and respiration represent typical physiological information contained in full-size patient monitors. A patient monitor may also be designed to display physiological information from one organ only; a full-size EEG monitor, for example, may display EEG signal information from even 64 measurement channels. The EEG monitors currently used in neurological and intensive care monitoring are either integrated full-size patient monitors or devices specifically designed to monitor EEG information only. Depending on the application, EEG monitors typically employ EEG signals measured from 4 to 32 measurement channels. The monitors derive several different variables or parameters from each of the measurement channels. For example, 8 EEG parameters may be derived from each measurement channel, whereby the total number of EEG parameters is between 32 and 256, depending on the number of the measurement channels. In addition, more EEG signals may be derived from the measured data by simple subtraction operations. For example, by subtracting the EEG signals of two measurement channels a new EEG signal representing the voltage difference between two measurement points is obtained. This possibility may vastly increase the amount of information obtained. The time evolutions of the parameters are typically displayed in trend-graphs, where time is displayed in the x-axis and the corresponding parameter value in the y-axis. The time axis shown is normally rather wide, between 2 and 48 hours.

Due to the limited size of the display of the monitor, all the information acquired from a subject cannot be displayed to the user at one time but the user must select the information to be displayed at each time through the user interface of the monitor. The information that is visible at one time on the screen of the display is in this context termed a screen page. The information that may be displayed to the user is thus divided between a plurality of screen pages. One of the screen pages is typically the default screen page and it includes information that is regarded as the most vital in view of the state of the subject. The default screen page is here termed the primary screen page, while the other screen pages that may be selected by the user are termed secondary screen pages. Various trend-graphs are typically displayed on the secondary screen pages and the user interface of the patient monitor is provided with tools, such as a menu system and/or a switch knob, for changing the screen page to be displayed at each time.

Consequently, the user has to browse the screen pages to find the information of his/her interest. The high amount of information included in the trend-graphs may, however, delay clinical decision-making, since the user has to browse several screen pages and since the monitor cannot assist the user for speeding up the discovery of the information that may be relevant at each time and before any limits of the alarming functionality are exceeded.

This drawback is further aggravated by the fact that part of the information related to the trend-graphs may be irrelevant, because some parameters are useful only within a specific etiology group of patients. Therefore, the user may have to find the relevant information from among information that may be more or less irrelevant. In addition, the selection of relevant information is slowed down by the fact that some parameters are affected only in rare occasions and remain unchanged most of the time.

Patient monitors are typically also furnished with the above-mentioned alarming functionality. Alarms are normally both audible and visual effects aiming to alert the nursing staff to a life-threatening condition or to another event considered vital. For example, a patient monitor alarms if arterial blood oxygen saturation drops below 90%. In most monitors, the alarm limits may be defined by the user, since the limits typically depend on patient etiology, age, gender, medication, and various other subjective factors. For example, upper limits for heart rate, indicating tachycardia, are higher in infants and children than in adults.

Various clinical decision support systems may also used to assist the physicians and the nursing staff in clinical decision-making. However, the use of fixed alarm limits or decision support systems cannot assist a clinician in detecting the less critical physiological changes and trends that may, in the course of time, lead to a life-threatening condition or to another vital change in the state of the patient. Furthermore, clinical decision support systems are complex and expensive, due to the embedded diagnostic intelligence.

BRIEF DESCRIPTION OF THE INVENTION

The above-mentioned problems are addressed herein which will be comprehended from the following specification.

In an embodiment, a method for monitoring the physiological state of a subject comprises acquiring a first plurality of physiological signals from a subject, determining a second plurality of signal parameters based on the first plurality of physiological signals, and producing signal information comprising at least one type of signal information selected from a group including (1) time series representative(s) for at least one signal parameter of the second plurality of signal parameters and (2) signal waveform(s) of at least one of the first plurality of physiological signals. The method further includes selecting relevant signal information from the signal information, displaying at least one screen page at a time, thereby to make at least part of the signal information visible to a user, and revising the signal information visible to the user on the at least one screen page, wherein the revising is performed in response to the selecting and without user interaction.

In another embodiment, an apparatus for monitoring the physiological state of a subject comprises a parameter determination unit configured to determine a second plurality of signal parameters from a first plurality of physiological signals acquired from the subject and a data processing unit configured to produce signal information comprising at least one type of signal information selected from a group including (1) time series representative(s) for at least one signal parameter of the second plurality of signal parameters and (2) signal waveform(s) of at least one of the first plurality of physiological signals. The apparatus further comprises a selection unit configured to select relevant signal information from the signal information, a display unit configured to display at least one screen page at a time to a user, thereby to make at least part of the signal information visible to the user, and a display control unit configured to revise, without user interaction, the signal information visible to the user on the at least one screen page, wherein the display control unit is responsive to the selection unit.

In a still further embodiment, a computer program product for monitoring the physiological state of a subject comprises a first program product portion configured examine whether any of a plurality of signal parameters derived from the subject is indicative of a relevant change in the state of the subject, wherein each signal parameter is derived from at least one physiological signal obtained from the subject and a second program product portion, responsive to the first program product portion, configured to revise, without user interaction, signal information currently visible to a user, wherein the signal information comprises at least one type of information selected from a group including (1) time series representative(s) for at least one signal parameter of the plurality of signal parameters and (2) signal waveform(s) of at least one of a plurality of physiological signals obtained from the subject.

Various other features, objects, and advantages of the invention will be made apparent to those skilled in the art from the following detailed description and accompanying drawings.

DETAILED DESCRIPTION OF THE INVENTION

Figure 1:
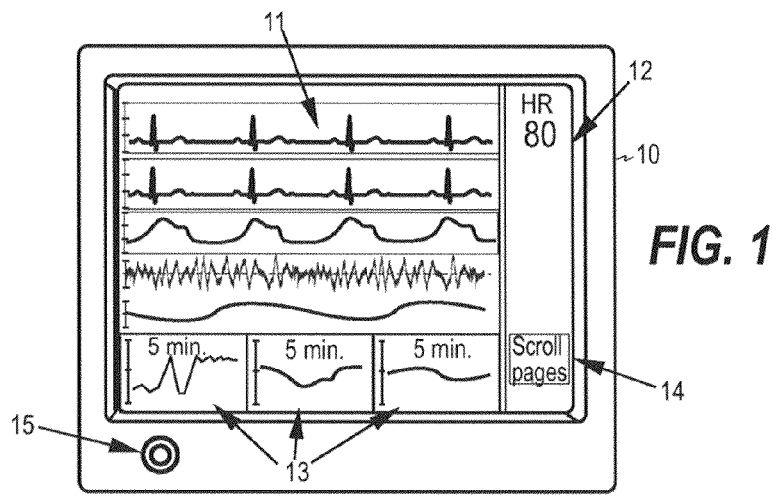
FIGS. 1 and 2 illustrate two typical screen pages of a patient monitor.
Figure 2:
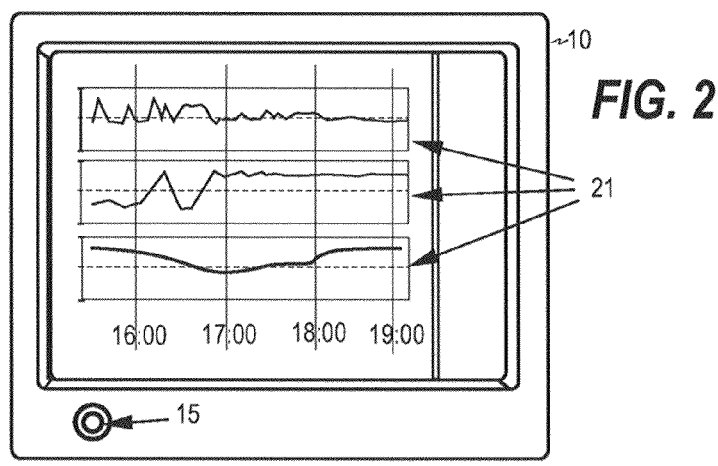

FIGS. 1 and 2 illustrate two screen pages of a multi-page patient monitor 10. As discussed above, in a multi-page monitor the information that may be displayed to the user is normally divided between a plurality of screen pages including a primary screen page displayed by default and multiple secondary screen pages that the user may select. FIG. 1 illustrates an example of the primary screen page, while FIG. 2 illustrates an example of a secondary screen page. The primary screen page typically presents waveforms 11 of a plurality of physiological signals, such as ECG, EEG, oxygen saturation, blood pressure, respiration, etc. The primary page typically also includes, for each waveform, a numerical information field 12 in which various information derived from each waveform may be presented. The primary screen may further include one or more mini-trend fields 13 each showing a short-time trend-graph of a physiological parameter measured from the subject. The monitor further includes user interface tools, such as a menu system 14 and/or a switch knob 15, for changing the screen page to be displayed. The secondary screen pages typically include trend-graphs for the different parameters defined in the monitor, which is why the said pages are also called trend pages. Through the user interface tools, the user may browse the trend-graphs derived from the physiological signals and select the trend pages of interest. FIG. 2 illustrates a secondary screen page including three trend-graphs 21 provided with a common time scale. The time scale typically covers a long time period, such as 2 to 48 hours. The trend pages thus show the waveform information in a compressed and refined form.

Figure 3:
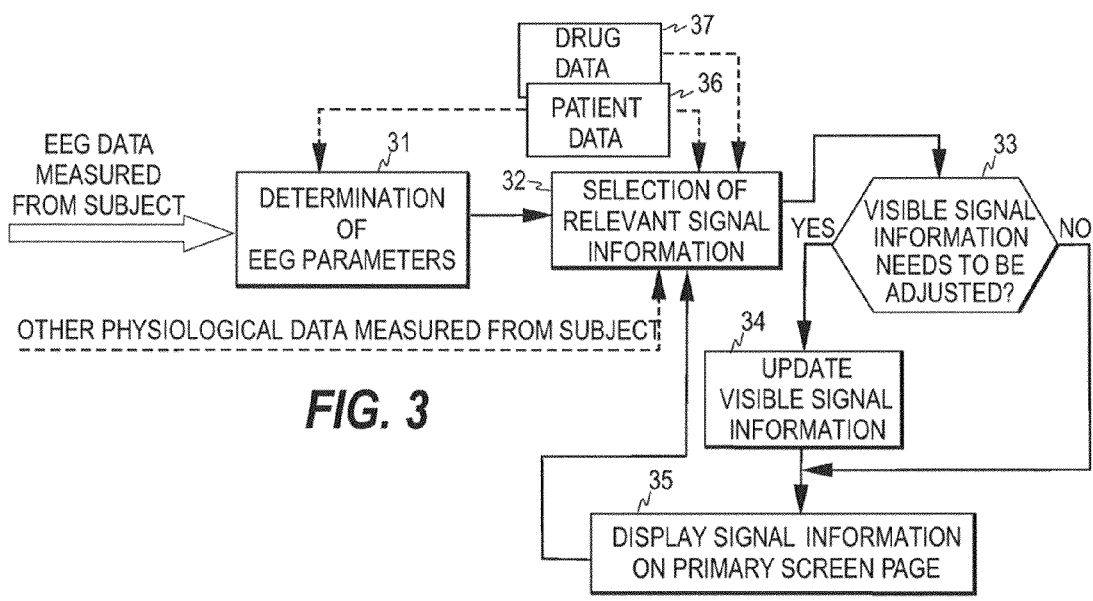
FIG. 3 is a flow diagram illustrating the selection of the information for the primary screen page of a monitor.

FIG. 3 illustrates an embodiment of a method for monitoring a subject through a patient monitor. Generally, a plurality of physiological signals are acquired from the subject, where one physiological signal corresponds to one measurement channel. The plurality of physiological signals may comprise one or more signal types, wherein one signal type refers to the physiological signals originating from one organ, such as brain. Below, EEG signal data is used as an example of the physiological signal data acquired from the subject and it is thus assumed below that the monitor is furnished with an EEG monitoring capability providing a plurality of EEG measurement channels. Based on the raw real-time EEG data obtained from the subject, a set of EEG signal parameters is determined for at least some of the measurement channels at step 31. A signal parameter here refers to a variable calculated from the waveform data of one or more of the physiological signals acquired from the subject. If a signal parameter is derived from more than one physiological signal, i.e. from more than one measurement channel, the said physiological signals are usually of the same signal type. Although a fixed number of parameters may be determined for each measurement channel, the number of signal parameters derived from a measurement channel may also depend on the channel in question. The total number of signal parameters derived from the plurality physiological signals may thus vary depending on the application.

Based on the latest signal parameters, the system determines the signal information that is currently relevant for the user to view (step 32). Signal information here refers generally to the information comprising the raw signal waveforms obtained from the subject and/or the time series of the signal parameters derived from the waveform data. That is, either or both the parameter trends and the signal waveforms may be presented to the user. The parameter trends may be presented in various forms, such as graphs, tables, or bar diagrams/graphs. A general term "time series representative" is therefore used for all representations of the trend (i.e. time series) of a signal parameter. It is assumed below that both types of signal information may be presented to the user and that the time series representatives of the signal parameters are in the form of trend-graphs.

The process then compares the relevant signal information with the signal information displayed currently to the user, thereby to check whether the signal information visible at the moment needs to be adjusted (step 33). If this is so, the visible signal information is updated (step 34) to display the relevant signal information, or part thereof, on the primary screen page (step 35). Thus, the signal information that is deemed as relevant at each time for the user to view is lifted to the topmost screen page so that the said information becomes visible to the user, if the said information is currently not visible. The above process is continuous, i.e. the selection of relevant signal information and the update of visible signal information are carried out substantially continuously based on the (real-time) time series of the signal parameters.

As discussed above, the number of parameters derived per channel may vary and some parameters may be derived using information from two or more waveforms. Such parameters may be indicative of coherence between two measurement sites, for example. The use of coherence parameters is discussed below in connection with the embodiments of FIG. 4.

At a certain point of time, the selection process, i.e. step 32, may thus determine that one or more of the EEG parameters or features defined in step 31 have changed so that the said parameter(s) assume(s) the status of relevant signal information. In response to this, the display is controlled, without user interaction, so that the said information becomes visible to the user. For example, the information displayed in one or more of the mini-trend fields 13 of the primary screen page may be changed so that the trend-graph(s) of the parameters that are currently regarded as relevant become visible to the user. This operation may be continuous so that the primary screen continuously displays the trend-graphs of the relevant parameters in the mini-trend fields. A new primary screen page including the trend-graphs of the said parameters may also be composed and displayed temporarily, or the secondary screen page that includes the relevant parameters may temporarily be given the status of the primary screen page and may thus be displayed temporarily. Furthermore, the system may decide in step 32 that one or more new waveforms are to be presented on the primary screen.

The automatic change of the visible signal information may be associated with an alarm signal, such as an audio alarm, and the default screen page may returned after user acknowledgment, for example. The selection process may also determine that none of the signal information is currently relevant, in which case the primary screen page remains unaltered. The selection process may also detect that the signal information considered as relevant is already visible to the user. In this case, the primary screen page may be left unaltered or the appearance thereof may be changed. For example, the order of the visible signal information on the screen may be changed. The change of the user view is thus conditional. The user view is changed if the signal information considered as relevant is not displayed currently or if the said information is not displayed in appropriate format.

The selection process 32 may further use subject-specific patient data 36 to find the EEG parameters that will probably be altered. This embodiment is useful particularly if a large number of parameters are to be derived from the physiological data. The patient data may include demographic data, etiologic data, reasons for hospital admission, results from medical (radiological, neurological, etc.) examinations, family history, genetic data, allergies, etc. The patient data may be retrieved automatically from clinical information system databases, and the parameters that are determined in step 31 may depend on the said data. Furthermore, drug data 37 may be utilized in the selection process. The drug data may be retrieved automatically from devices controlling the administration of drugs, such as infusion pumps and/or valves controlling the exhaled gas concentrations. The drug data may also include the pharmacodynamic and pharmacokinetic properties of the drugs administered. Other physiological parameters may also be utilized in the selection process. For example, heart rate and/or heart rate variability measured from an ECG signal may be utilized in the identification of epileptic activity and thus as indicators that guide in possible selection of EEG parameters indicative of epileptiform activity. Alternatively, brain oxygen saturation measured by near-infrared spectroscopy, for example, may be utilized as an aid in the selection process.

By automatically adjusting or changing the signal information visible to the user, the detection of a change in the state of a subject, and thus also clinical decision-making, may be accelerated. Furthermore, the possibility of undetected changes in the state of the subject may be reduced. Although the actual adjusting or changing of the visible signal information is automatic and occurs without user interaction, the selection algorithm may be provided with user-definable options that define the operation of the selection process.

Figure 4:
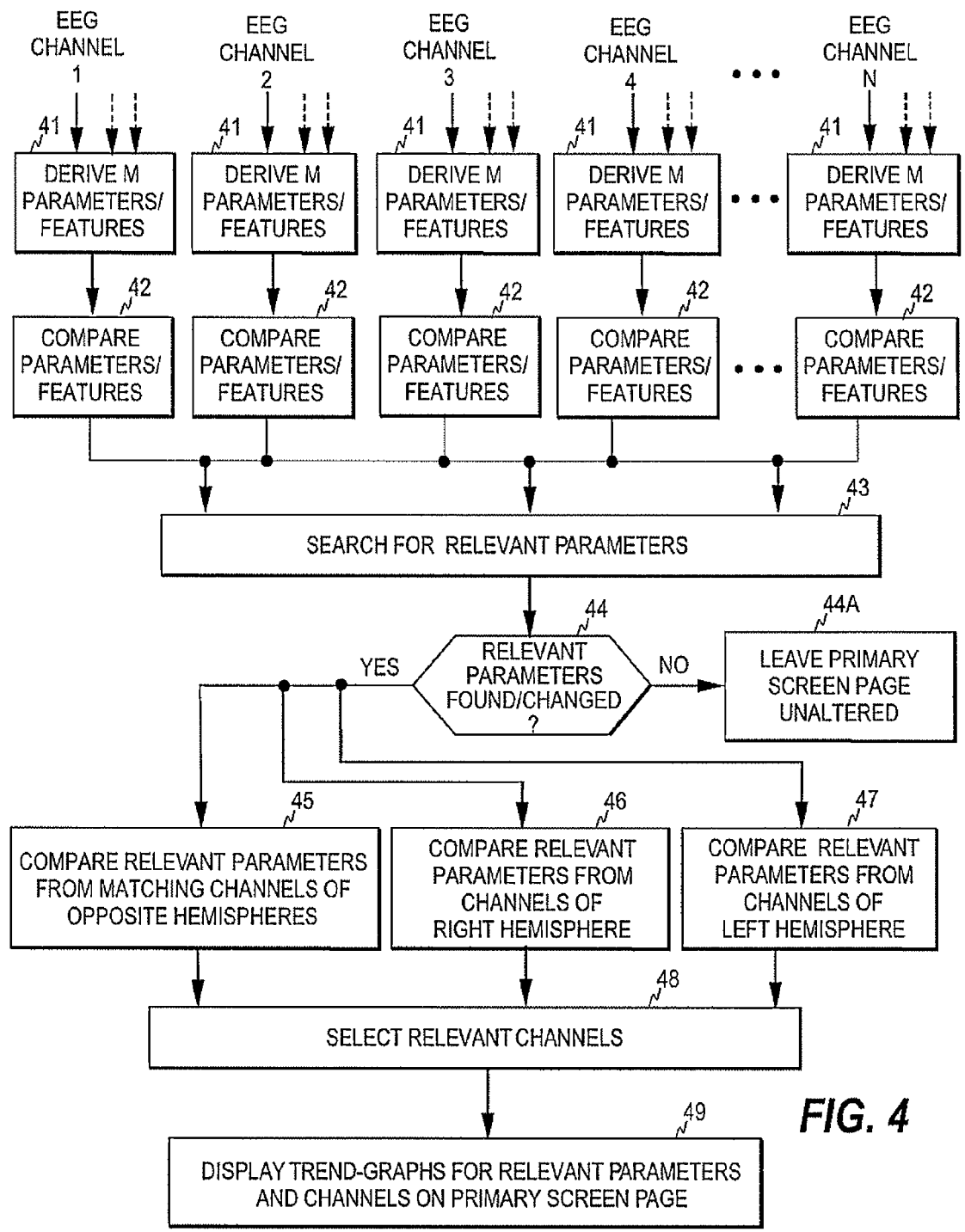
FIG. 4 illustrates embodiments of the selection process of FIG. 3.

FIG. 4 illustrates an embodiment of the selection process of FIG. 3. It is assumed here that N EEG channels are obtained from the subject. For each channel, M signal parameters/features are then derived (steps 41) for each consecutive time window and the M parameters that are substantially concurrent are compared with each other (steps 42) or to predetermined threshold values to find out whether any one or more of the signal parameters indicate a significant change in the status of the subject. Based on the comparisons, relevant signal parameters are searched for at step 43. If at least one new relevant parameter is found, i.e. if one or more of the parameters indicate a significant change in the current status of the subject, the selection process may further examine whether the change is concentrated on a particular scalp area. For this, the selection process may compare the relevant parameters derived from matching channels of opposite hemispheres (step 45), from channels of right hemisphere (step 46), and from channels of left hemisphere (step 47), for example. Based on the comparison, the process selects the measurement channels on which the relevant parameters show the most significant changes. The parameters of these channels are then selected as the relevant signal information and the trend-graphs of the said parameters are displayed on the primary screen page (steps 48 and 49). Thus, in this case the relevant signal information comprises relevant parameters from scalp areas in which the said parameters show the most significant changes.

If no relevant parameter is found in step 44, the primary screen page is left unaltered. In steps 45 to 48, the scalp area with the most significant changes was searched for. However, the localization of the most significant changes does not necessarily require separate steps but the said areas may also be determined by calculating correlation properties of the different channels, for example. In this embodiment, steps 45 to 48 are thus omitted and several input channels are supplied to each step 41, as is shown by dashed input arrows in the figure. In each step 41, one or more signal parameters may be derived, each signal parameter including inter-channel information, such as coherence between measurement channels. The signal parameters are then compared with each other to find out the relevant parameters. For this, steps 42 and 43 may be combined, so that desired signal parameters may be compared with each other.

In EEG monitoring, a wide variety of changes may take place in the raw EEG signal data obtained from the subject. However, there are normally only one or at most a few optimal parameters for the monitoring of each of these changes. For example, in case of oxygen supply break, EEG amplitude decreases and in case of epileptic activity specific waveforms including spiky patterns will appear. Although there are optimal parameters for both of these cases, these parameters are more or less irrelevant information in other cases, such as when monitoring the level of sedation/anesthesia or the degree of metabolic encephalopathy, or in case of patients in the so-called alpha-coma state. Consequently, the number of parameters that may simultaneously be relevant for each subject is normally so low that the trend-graphs of the said parameters may be presented on one screen page or in the mini-trend fields of the primary screen page.

Figure 5:
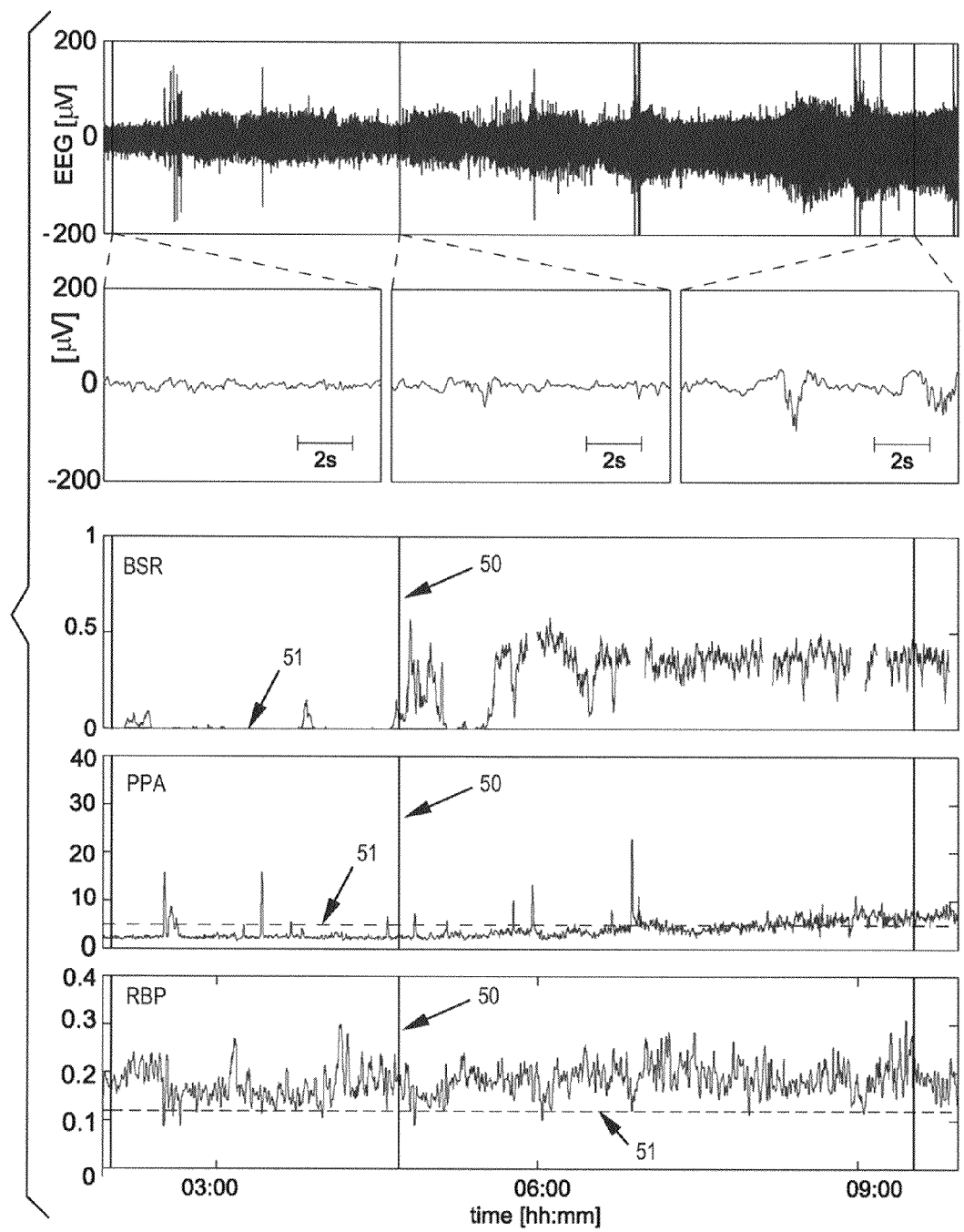
FIG. 5. illustrates an example of the behaviour of three different EEG parameters in case of a post cardiac arrest patient.

FIG. 5 illustrates an 8-hour EEG recording from a post cardiac arrest patient, together with the trend-graphs of three EEG parameters. Generally, the state of a comatose patient may be categorized into six different categories according to the patterns present in the EEG waveform: delta/theta activity, triphasic waves, burst-suppression pattern (BSP), alpha/theta/spindle coma, epileptiform activity, and amplitude attenuation. Delta/theta activity is regarded as the least critical state and generally the criticality increases in the above order, i.e. amplitude attenuation is normally the most critical state. Typical transitions occur, for example, from delta/theta activity to amplitude attenuation (hypoxic/ischemic brain injuries) or to triphasic waves (hepatic encephalopathy) when the state of the patient takes a turn for the worse. The three lowermost epochs of FIG. 5 illustrate, respectively, three parameters that may be used to detect the above transitions: burst-suppression ratio (BSR) shown in the middle of the figure, peak-to-peak RMS amplitude (PPA) shown in the second graph from the bottom), and relative band power (RBP) shown in the lowermost graph. The peak-to-peak RMS amplitude is calculated by taking the RMS (root mean square) of all absolute differences between adjacent positive and negative peaks over a segment of data. The relative power is derived from a frequency band of 3 Hz to 4.8 Hz. The BSR may be used to discriminate the BSP state from the other states, the PPA may be used to detect a transition from delta/theta activity to amplitude attenuation, and the RBP may be used to detect a transition from delta/theta activity to triphasic waves or to epileptiform activity. The dashed horizontal lines 51 shown in the figure are threshold values set for the parameters. Zero may be used as the threshold value for the BSR. When the threshold is significantly passed to either side, the parameter indicates a probable change in the EEG classification.

The selection criteria used to select the relevant signal information in steps 32 and 43 may thus be based on predetermined threshold values 51 for the parameters, which need to be exceeded or underset before a parameter is regarded as a relevant parameter. Short-time fluctuations of the parameter values may be filtered out to prevent the relevant signal information from changing in an instable manner. The selection criteria may utilize simple binary logic as described above. However, in an advanced form the selection criteria may also utilize other logic types, such as fuzzy logic or Bayesian logic. In fuzzy logic, the decision is not based on precise TRUE (1) and FALSE (0) statements as in binary logic, but on class membership values which are between 0 and 1. Alternatively, or in addition, the selection criteria may be based on the variability and/or dynamic range of an EEG parameter over a certain time period.

Figure 6:
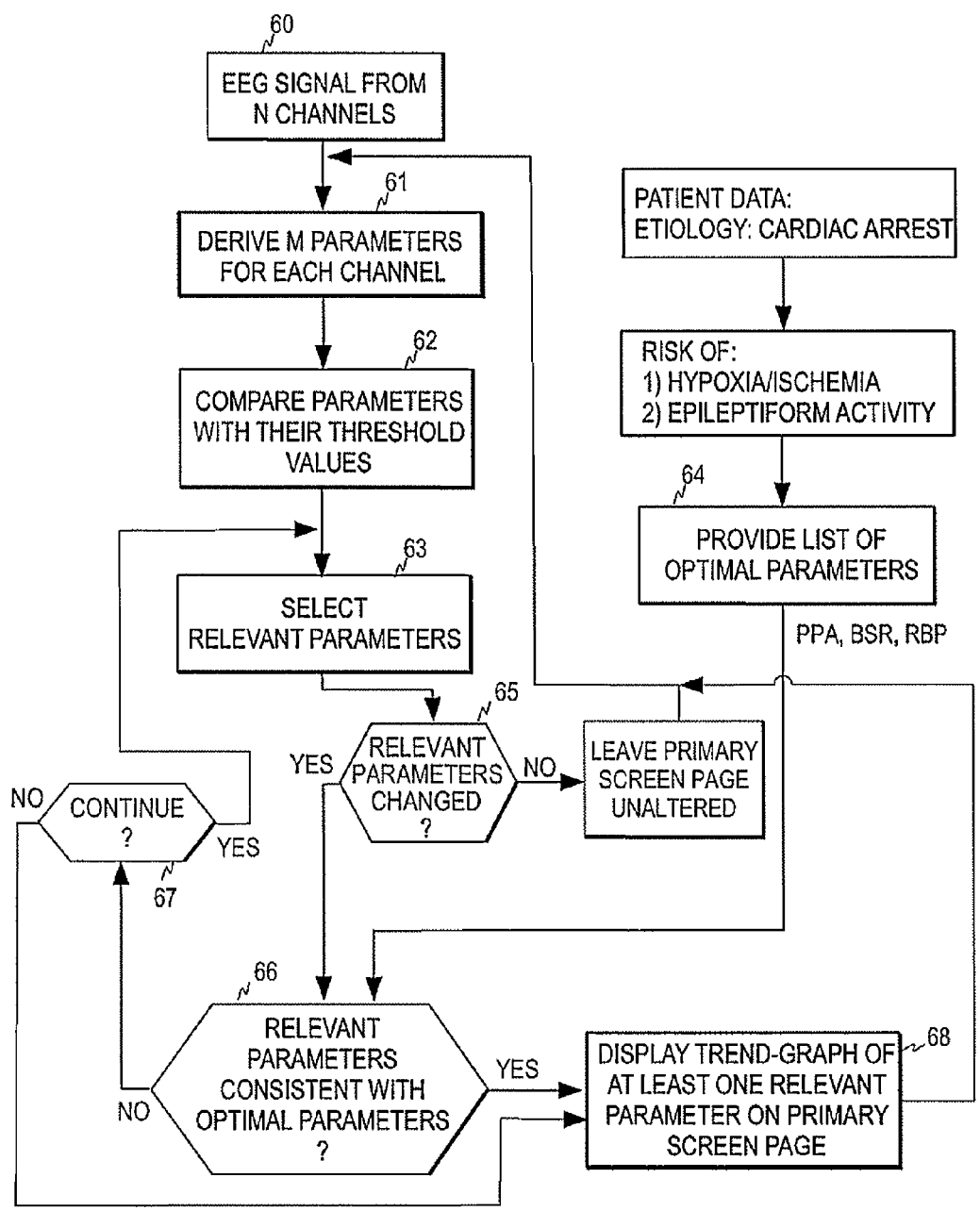
FIG. 6 is a flow diagram illustrating an embodiment of the selection process that may be used in connection with the EEG parameters of FIG. 5.

FIG. 6 illustrates a further example of the selection process. In steps 60 and 61, M parameters are derived for each measurement channel. It is assumed here that the parameters include the three parameters of FIG. 5 and that the same patient is in question. In this case, the subject-specific patient data 36 would therefore indicate that the risks related to the subject include hypoxia/ischemia and epileptiform activity, as is shown in the top right corner of FIG. 6. Based on the patient data and the said risks, a list of optimal parameters may be searched for. In this case the list would thus include the parameters shown in FIG. 5, i.e. PPA, BSR, and RBP. In steps 62 and 63, the parameters derived from the EEG raw data are compared with their respective thresholds and the relevant parameters are selected based on the comparisons made. In case of FIG. 5, the comparisons made before time instant 50 would indicate that BSR remains predominantly at zero (no burst suppression patterns), that PPA remains predominantly below the respective threshold (i.e. amplitude attenuation is present), and that RBP remains predominantly above the respective threshold (i.e. epileptiform activity is present). Therefore, PPA and RBP would be chosen as relevant parameters in step 63, while BSR would not be regarded as a relevant parameter. However, after time instant 50 the same comparisons indicate mostly that BSR is above the threshold (burst-suppression patterns present), that PPA is near the threshold, and that RBP remains predominantly above the respective threshold. Therefore, BSR and RBP would be chosen as relevant parameters, while PPA would not be regarded as a relevant parameter anymore, despite the moderate attenuation indicated by PPA. If fuzzy logic is applied to this example, EEG signal burst-suppression and epileptiform activity class membership values are close to 1 after time instant 50, whereas amplitude attenuation class membership value is close to 0.5. Therefore, BSR and RBP are again selected as relevant parameters.

If it is detected at step 65 that the relevant parameters have changed, the selection process may check at step 66 if the new relevant parameters are consistent with the optimal parameters selected in step 64 based on the patient data. If this is the case, the information to be displayed is changed by presenting, for example, the trend-graphs of the relevant parameters on the primary screen page (step 68). The check may simply include a comparison whether the relevant parameters belong to the group of optimal parameters selected in step 64. If consistency is not found, the process may repeat the selection one or more times until consistency is found (steps 63, 65, 66, and 67). If consistency is not found after a predetermined number of selection steps, the trend-graphs may still be displayed (step 68) for at least those parameters that belong to the group of optimal parameters. If relevant parameters are not found or if the relevant parameters have not changed, the primary screen page is left unaltered.

Figure 7:
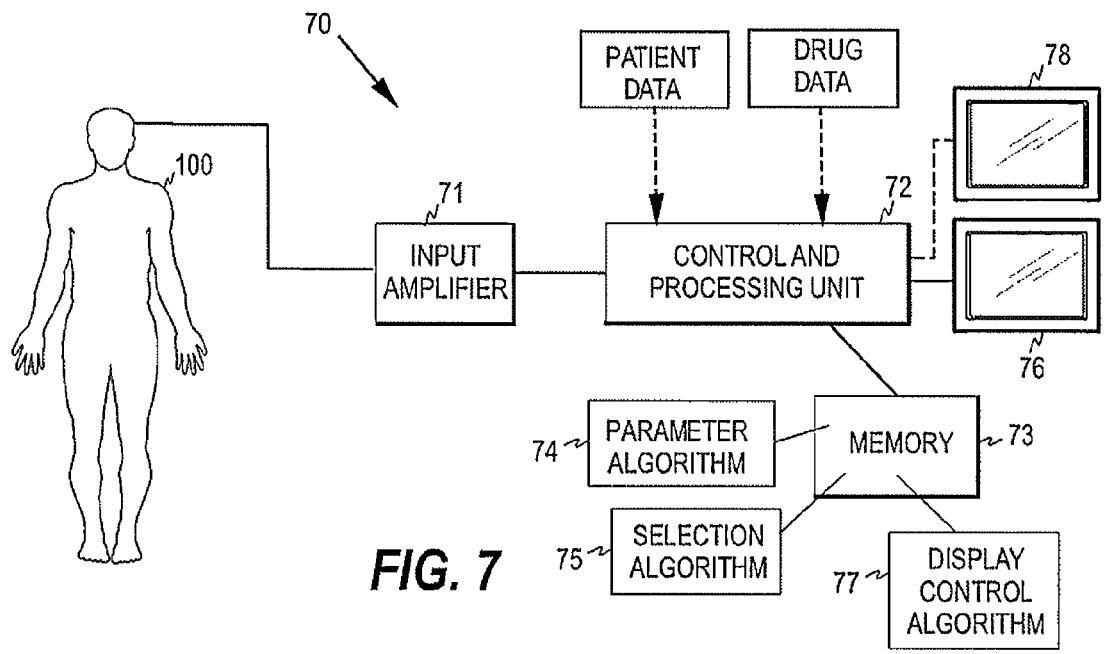
FIG. 7 illustrates an apparatus or system for monitoring a subject.

FIG. 7 illustrates one embodiment of a monitoring apparatus 70 for monitoring a subject 100. As discussed above, the type of the physiological signal data measured from the subject may vary, and may be, for example, EEG data. The measured physiological signals are supplied to a control and processing unit 72 through an input amplifier 71. The control and processing unit converts the signals into digitized format for each measurement channel. The digitized signal data may then be stored in the memory 73 of the control and processing unit. The digitized signal data may be utilized by a parameter algorithm 74 adapted to record, when executed by the control and processing unit, the time series of each parameter for each measurement channel. The time series of the parameters may be stored in memory 73.

The control and processing unit is further provided with a selection algorithm 75 adapted to select, when executed by the control and processing unit, the relevant signal information for the primary screen page of the monitor. The control and processing unit is further configured to control the display unit 76 of the monitor based on the selections made by the selection algorithm. As discussed above, this may involve changing the information content of the primary screen page, changing the screen page visible to the user, composing a new page to be displayed to the user, or adjusting the appearance of the visible signal information. The display control algorithm 77 may be stored in the memory of the control and processing unit.

It is assumed above that the monitoring apparatus comprises only one display screen. However, the apparatus may also be provided with multiple display units, thereby to increase the amount of information that may be displayed at one time. Consequently, the number of default screen pages may be higher than one. For example, the apparatus may have two display screens, as display screens 76 and 78 in FIG. 7, one displaying the first primary screen page and another displaying the second primary screen page. The first primary screen page may include waveforms for a plurality of physiological signals, while the second primary page may include one or more trend-graphs, for example. In response to a change of the relevant signal information, the multiple display units may display new waveforms and/or trend-graphs, or adjust the appearance of the signal information currently visible. The corresponding change in the status of the subject may also be presented on more than one screen pages. For example, the first primary screen page may present the trend of a relevant parameter in one or more of its mini-trend fields, while the secondary screen page may present the trend of the same parameter using a wider time scale, for example. That is, the update of the visible signal information may concern several display units.

Figure 8:
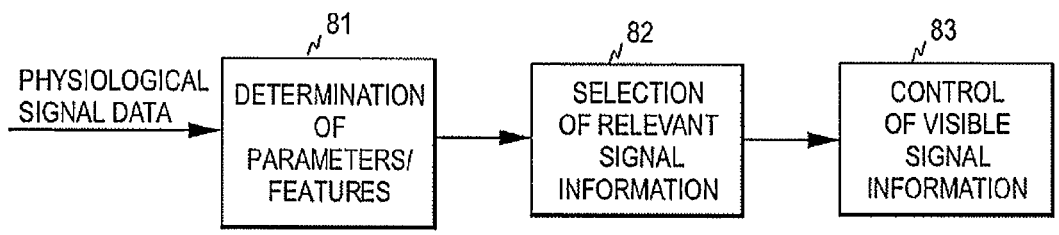
FIG. 8 illustrates the operational entities of the control and processing unit of FIG. 7.

Regardless of the number of display units, the control and processing unit, which is adapted to execute the above-described algorithms, may be seen as an entity of three operational modules or units, as is illustrated in FIG. 8: a parameter determination unit 81 configured to determine the time series of the parameters/features for the measurement channels, a selection unit 82 configured to select the relevant signal information from among the signal information produced, and a display control unit 83 configured to revise or adjust the signal information visible to the user based on the relevant signal information and without user interaction. The display control unit may drive multiple display units and user preferences may affect the operation of each unit.

A conventional patient monitor may be upgraded to enable the monitor to control the signal information visible to the user on the primary screen page. Such an upgrade may be implemented, for example, by delivering to the monitor a software module that enables the monitor to select the relevant signal information and to change the signal information to be displayed to the user. The software module may be delivered, for example, on a data carrier, such as a CD or a memory card, or the through a telecommunications network. Since the software module may utilize the signal parameters determined by the monitor, the module does not necessarily comprise more than two portions: a first program product portion configured examine whether any of the said signal parameters is indicative of a relevant change in the state of the subject and a second program product portion, responsive to the first program product portion, configured to adjust or revise the signal information currently visible to the user. However, the software module may also determine one or more of the signal parameters/features, especially if all signal parameters are not available in the monitor.

The monitor may also be a single page monitor in which some of the signal information is made visible only if the said information is considered as relevant signal information. Further, the signal information produced for the display unit(s) may also comprise the time series of the signal parameters only. That is, the monitor may display trend-graphs only, not waveforms of the physiological signals. Similarly, it is possible that the monitor does not display parameter trend-graphs, but signal waveforms only. However, even though the parameter trend-graphs are not presented, the signal parameters need to be derived from the waveform data, since the revising of the visible waveforms is based on the parameters.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for monitoring the physiological state of a subject, the method comprising:
   acquiring EEG signals from a subject, wherein a first plurality of EEG signals are acquired from a left hemisphere and a second plurality of EEG signals are acquired from a right hemisphere;
   determining a third plurality of EEG signal parameters and a fourth plurality of EEG signal parameters, wherein the third plurality of EEG signal parameters are based on the first plurality of EEG signals and the fourth plurality of EEG signal parameters are based on the second plurality of EEG signals;
   producing signal information comprising at least one type of signal information selected from a group including (1) time series representatives for each of the third plurality of EEG signal parameters and for each of the fourth plurality of EEG signal parameters; and (2) signal waveforms of the first plurality of EEG signals and of the second plurality of EEG signals;
   selecting relevant signal information from the signal information by comparing the third plurality of EEG signal parameters with each other and by comparing the fourth plurality of EEG signal parameters with each other, wherein at least one EEG signal parameter is selected as the relevant signal information, wherein the selected at least one EEG signal parameter belongs to the third plurality of EEG signal parameters or to the fourth plurality of EEG signal parameters;
   defining a set of optimal parameters from the third plurality of EEG signal parameters and from the fourth plurality of EEG signal parameters based on subject-specific patient data;
   examining whether the set of optimal parameters is consistent with the at least one EEG signal parameter selected as the relevant signal information;
   displaying a primary screen page, thereby to make at least part of the signal information visible to a user; and
   revising the signal information visible to the user on the primary screen page to display the selected relevant signal information, wherein the revising is performed in response to the examining and without user interaction.

2. The method according to claim 1, wherein the revising includes changing at least one time series currently visible to the user.

3. The method according to claim 1, wherein the revising includes making at least one signal waveform visible to the user.

4. The method according to claim 1, wherein the revising includes changing the primary screen page currently displayed.

5. The method according to claim 1, wherein the selecting includes comparing at least some of the third plurality of EEG signal parameters and at least some of the fourth plurality of EEG signal parameters with predetermined threshold values.

6. The method according to claim 1, wherein the revising includes changing appearance of the signal information currently visible to the user on the primary screen page.

7. The method according to claim 1, wherein the selecting further includes selecting relevant signal information by comparing the third plurality of EEG signal parameters and the fourth plurality of EEG signal parameters with each other.

8. The method according to claim 1, wherein
the determining includes determining a fifth plurality of EEG signal parameters based on EEG signals of a particular area of the left hemisphere and the right hemisphere;
the producing includes producing signal information comprising time series representatives for each of the fifth plurality of EEG signal parameters; and
the selecting includes selecting relevant signal information by comparing the third plurality of EEG signal parameters, the fourth plurality of EEG signal parameters and the fifth plurality of EEG signal parameters with each other.

9. A monitoring device for monitoring the physiological state of a subject, the monitoring device comprising:
a parameter determination unit configured to determine a third plurality of EEG signal parameters from a first plurality of EEG signals acquired from a left hemisphere of a subject and a fourth plurality of EEG signal from a second plurality of EEG signals acquired from a right hemisphere of the subject;
a data processing unit configured to produce signal information comprising at least one type of signal information selected form a group including (1) time series representative for each of the third plurality of EEG signal parameters and for each of the fourth plurality of EEG signal parameters; and (2) signal waveforms of the first plurality of EEG signals and of the second plurality of EEG signals;
a selection unit configured to select relevant signal information from the signal information by comparing the third plurality of EEG signal parameters with each other and by comparing the fourth plurality of EEG signal parameters with each other,
wherein the selection unit is further configured to select at least one EEG signal parameter as the relevant signal information,
wherein at least one EEG signal parameter belongs to the third plurality of EEG signal parameters or the fourth plurality of EEG signal parameters;
wherein the selection unit is further configured to define a set of optimal parameters from the third plurality of EEG signal parameters and from the fourth plurality of EEG signal parameters based on subject-specific patient data and to examine whether the set of optimal parameters is consistent with the at least one EEG signal parameter selected as the relevant signal information;
a display control unit configured to revise, without user interaction, the signal information visible to the user on the primary screen page,
wherein the display control unit is responsive to the selection unit.

10. The monitoring device according to claim 9, wherein the display control unit is configured to change at least one time series currently visible to the user.

11. The monitoring device according to claim 9, wherein the display control unit is configured to change the primary screen page currently displayed.

12. The monitoring device according to claim 9, wherein the selection unit is configured to compare at least some of the third plurality of EEG signal parameters and at least some of the fourth plurality of EEG signal parameters with predetermined threshold values.

13. The monitoring device according to claim 9, wherein the display control unit is configured to change appearance of the signal information currently visible to the user on the primary screen page.

14. A non-transitory computer program product for monitoring the physiological state of a subject, the computer program product comprising:
a first program product portion configured to define a set of optimal parameters from a third plurality of EEG signal parameters and from a fourth plurality of EEG signal parameters based on subject-specific patient data, wherein the third plurality of EEG signal parameters are derived from a first plurality of EEG signals obtained from a left hemisphere of the subject and the fourth plurality of EEG signal parameters are derived from a second plurality of EEG signals obtained from a right hemisphere of the subject;
a second program product portion responsive to the first program product portion, configured to examine whether any of the set of optimal parameters from the third plurality of EEG signal parameters or any of the set of optimal parameters from the fourth plurality of EEG signal parameters are indicative of a relevant change in the state of the subject, wherein the third plurality of EEG signal parameters are derived from a first plurality of EEG signals obtained from a left hemisphere of the subject and the fourth plurality of EEG signal parameters are derived from a second plurality of EEG signals obtained from a right hemisphere of the subject; and
a third program product portion, responsive to the second program product portion, configured to revise, without user interaction, signal information currently visible to a user, wherein the signal information comprises at least one type of information selected from a group including (1) time series representatives for each of the set of optimal parameters from the third plurality of EEG signal parameters and for each of the set of optimal parameters from the fourth plurality of EEG signal parameters; and (2) signal waveforms of the first plurality of EEG signals and of the second plurality of EEG signals obtained from the subject.

15. The non-transitory computer program product according to claim 14, further comprising a fourth program product portion configured to determine at least some of the third plurality of EEG signal parameters from the first plurality of EEG signals and at least some of the fourth plurality of EEG signal parameters from the second plurality of EEG signals.

* * * * *